(12) United States Patent
Hoshika

(10) Patent No.: US 9,272,478 B2
(45) Date of Patent: Mar. 1, 2016

(54) APPARATUS FOR REDUCING THE THICKNESS OF AN ABSORBENT BODY AND METHOD OF THE SAME

(75) Inventor: Kazuhiko Hoshika, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 211 days.

(21) Appl. No.: 13/980,395

(22) PCT Filed: Jan. 13, 2012

(86) PCT No.: PCT/JP2012/050589
§ 371 (c)(1),
(2), (4) Date: Nov. 12, 2013

(87) PCT Pub. No.: WO2012/099015
PCT Pub. Date: Jul. 26, 2012

(65) Prior Publication Data
US 2014/0182462 A1    Jul. 3, 2014

(30) Foreign Application Priority Data
Jan. 20, 2011  (JP) .................................. 2011-010063

(51) Int. Cl.
B30B 3/04       (2006.01)
A61F 13/15      (2006.01)
B30B 15/00      (2006.01)
B21B 37/16      (2006.01)
B30B 15/30      (2006.01)

(52) U.S. Cl.
CPC .............. *B30B 3/04* (2013.01); *A61F 13/15617* (2013.01); *A61F 13/15707* (2013.01); *A61F 13/15772* (2013.01); *B30B 15/00* (2013.01); *B21B 37/165* (2013.01); *B30B 15/308* (2013.01)

(58) Field of Classification Search
CPC .................... A61F 13/15707; A61F 13/15772; A61F 2013/16; A61F 13/00987; A61F 13/00995; A61F 13/15585; A61F 13/15642; A61F 13/15715; A61F 13/1578; A61F 13/15788; B21B 37/165
USPC ........................... 100/41, 43, 47, 48; 700/155
See application file for complete search history.

(56) References Cited

U.S. PATENT DOCUMENTS 3,648,496 A * 3/1972 Petry et al. ..................... 72/11.8
4,398,254 A * 8/1983 Kondo et al. .................. 700/155

(Continued)

FOREIGN PATENT DOCUMENTS

CN        1950190 A     4/2007
JP        6205805 A     7/1994

(Continued)

OTHER PUBLICATIONS

International Search Report corresponding to PCT/JP2012/050589 dated Mar. 13, 2013. English translation.

(Continued)

*Primary Examiner* — Alexander P Taousakis
*Assistant Examiner* — Leonel Vasquez
(74) *Attorney, Agent, or Firm* — Hauptman Ham, LLP (57) ABSTRACT

Provided is an apparatus for reducing a thickness of an absorbent body having liquid absorbent fiber as a main material. The apparatus includes a pressing device that reduces the thickness of the absorbent body transported in a transport direction, by sandwiching and pressing the absorbent body in a thickness direction orthogonal to the transport direction, a pair of rollers that are positioned on a downstream side of the pressing device along the transport direction, and rotate while passing the absorbent body through a gap formed by outer circumferences of the pair of rollers opposing each other, a sensor that outputs measurement information relating to the thickness of the absorbent body at a position between the pressing device and the pair of rollers, and a controller that sets a size of the gap between the pair of rollers based on the measurement information.

7 Claims, 3 Drawing Sheets

(56) References Cited

U.S. PATENT DOCUMENTS

| | | | | |
|---|---|---|---|---|
| 4,768,433 | A | * | 9/1988 | Boissevain .................... 100/328 |
| 2005/0145317 | A1 | * | 7/2005 | Yamamoto .................... 156/73.5 |
| 2007/0251643 | A1 | | 11/2007 | Umebayashi et al. |

FOREIGN PATENT DOCUMENTS

| | | | |
|---|---|---|---|
| JP | 06205805 | A | 7/1994 |
| JP | 10323368 | A | 12/1998 |
| JP | 1133054 | A | 2/1999 |
| JP | 11033054 | A | 2/1999 |
| JP | 3519094 | B2 | 4/2004 |
| JP | 2004298413 | A | 10/2004 |

OTHER PUBLICATIONS

Office Action issued Jul. 3, 2014, corresponds to Chinese patent application No. 201280005823.2.

Office Action issued Mar. 9, 2015, corresponding to Chinese patent application No. 201280005823.2.

* cited by examiner

FIG. 1A

FIG. 1B
B-B SECTION

FIG. 1C
C-C SECTION

FIG. 1D
D-D SECTION

APPARATUS FOR REDUCING THE THICKNESS OF AN ABSORBENT BODY AND METHOD OF THE SAME

RELATED APPLICATIONS

The present application is a National Phase of PCT/JP2012/050589, filed Jan. 13, 2012, and is based on, and claims priority from, Japanese Application No. 2011-010063 filed Jan. 20, 2011.

TECHNICAL FIELD

The present invention relates to an apparatus and method for reducing the thickness of an absorbent body of an absorbent article such as a disposable diaper.

BACKGROUND ART

Conventionally, disposable diapers, sanitary napkins and the like are known as examples of an absorbent article that absorbs excretory fluid and the like. Such absorbent articles usually include an absorbent body that absorbs the aforementioned liquid. And this absorbent body has a layered body having pulp fiber as liquid absorbing fiber layered in a predetermined form and a liquid permeable sheet such as tissue paper and the like that covers the outer circumference of this layered body.

CITATION LIST

Patent Literature

[PTL 1] Japanese Patent Application Laid-open Publication No. H06-205805

SUMMARY OF INVENTION

Technical Problem

Such an absorbent body 1 is, for example, manufactured in the following way (see FIG. 1A).

First, pulp fibers are layered, intermittently along the transport direction in approximately block forms, at approximately the center in the width direction of the carrier sheet 5a (this is a sheet that becomes the aforementioned liquid permeable sheet in the end, but is a continuous sheet at this point) that is continuously transported in the transport direction. And the surfaces of the layered bodies 3, 3 . . . in approximately block forms have the end portions in the width direction of the carrier sheet 5a in covered states thereby creating a continuous body of absorbent bodies 1a composed of a plurality if absorbent bodies 1, 1 . . . arranged continuously in the transport direction. Next, the continuous body of absorbent bodies 1a, by passing through a gap of the pressing device (not shown) along the transport direction, have the absorbent bodies 1 sandwiched and pressed from the up-down direction being the thickness direction at the space. And finally, the continuous body of absorbent bodies 1a are cut at a predetermined pitch at the cutting device (not shown) downstream in the transport direction to hereby produce the absorbent body 1 in a single product form being in a completed state usable as the aforementioned absorbent article.

Here, when the thickness of the absorbent body 1 after passing through the pressing device is not within the target range (target value plus or minus tolerance), the absorbent article manufactured using the absorbent body 1 becomes a defective product. Therefore, at the time of starting the manufacturing line, absorbent articles are temporary manufactured as a test run and the pressing device is adjusted so that the thickness of the absorbent body 1 is within the target range by measuring the thickness of the absorbent body 1 of the temporarily manufactured absorbent article and sequentially adjusting the dimension of the aforementioned gap of the pressing device in a trial-and-error manner.

However, since this adjustment is conducted in a trial-and-error manner as explained above, the adjustment takes time and the absorbent articles created during the adjustment cannot be used as a product and are discarded, resulting in reduction of the manufacturing yield.

The present invention has been made in view of conventional problems such as those mentioned above, and an object thereof is to alleviate the burdens when adjusting the pressing device and reduce the number of absorbent articles discarded at the time of adjustment, while allowing to reduce the number of defective products due to thickness failures of the absorbent body in an apparatus and method for reducing the thickness of absorbent bodies.

Solution to Problem

In order to solve the above-described problem, a principal aspect of the invention is, an apparatus for reducing a thickness of an absorbent body having liquid absorbent fiber as a main material, including:

a pressing device that reduces the thickness of the absorbent body transported in a transport direction, by sandwiching and pressing the absorbent body in a thickness direction orthogonal to the transport direction;

a pair of rollers that is positioned on a downstream side along the transport direction than the pressing device, and rotates while passing the absorbent body through a gap formed by outer circumferences of the pair of rollers opposing each other;

a sensor that outputs measurement information relating to the thickness of the absorbent body at a position between the pressing device and the pair of rollers; and a controller that sets a size of the gap between the pair of rollers based on the measurement information.

Further a method for reducing a thickness of an absorbent body having liquid absorbent fiber as a main material, including:

reducing a thickness of the absorbent body transported in a transport direction, by sandwiching and pressing the absorbent body in a thickness direction orthogonal to the transport direction;

passing the absorbent body through a gap between a pair of rollers that are positioned on a downstream side along the transport direction than the pressing device, and that have outer circumferences of the pair of rollers opposing each other;

outputting by a sensor, measurement information relating to the thickness of the absorbent body at a position between the pressing device and the pair of rollers; and setting a size of the gap based on the measurement information when the absorbent body is passed through the gap between the pair of rollers.

Features of the invention other than the above will become clear from the description of the present specification and the drawings attached.

Advantageous Effects of Invention

According to the present invention, the burdens on adjusting the pressing device are alleviated and the number of absorbent articles discarded at the time of this adjustment is reduced, while allowing to reduce the number of defective products due to thickness failures of the absorbent body in an apparatus and method for reducing the thickness of absorbent bodies.

DESCRIPTION OF EMBODIMENTS

At least the following matters will become clear from the description of the present specification with reference to the accompanying drawings.

A manufacturing apparatus for reducing a thickness of an absorbent body having liquid absorbent fiber as a main material, including:

a pressing device that reduces the thickness of the absorbent body transported in a transport direction, by sandwiching and pressing the absorbent body in a thickness direction orthogonal to the transport direction;

a pair of rollers that is positioned on a downstream side along the transport direction than the pressing device, and rotates while passing the absorbent body through a gap formed by outer circumferences of the pair of rollers opposing each other;

a sensor that outputs measurement information relating to the thickness of the absorbent body at a position between the pressing device and the pair of rollers; and a controller that sets a size of the gap between the pair of rollers based on the measurement information.

According to such a thinning apparatus for reducing the thickness of absorbent bodies, the size of the gap between a pair of rollers is set based on measurement information relating to the thickness of the absorbent body after being sandwiched and pressed with the pressing device. Therefore, when the thickness of the absorbent body after being sandwiched and pressed with the pressing device is greater than the target range, the absorbent body can be thinned by sandwiching and pressing with a pair of rollers and resultantly reduce defective products due to thickness failures of the absorbent body.

Additionally, by thinning the absorbent body with a pair of rollers as above, the thickness of the absorbent body can be kept within the target range so that the pressing apparatus need not be finely adjusted and the number of absorbent articles discarded associated with the adjustment can be reduced.

In the thinning apparatus for reducing the thickness of absorbent bodies, it is preferable that the controller sets the size of the gap in such a manner that the absorbent body that passes through the gap is sandwiched and pressed by the pair of rollers, when a thickness indicated by the measurement information is greater than a target range of the thickness of the absorbent body.

According to such a thinning apparatus for reducing the thickness of absorbent bodies, the number of defective products due to the thickness of the absorbent body exceeding the target range can be reduced.

In the thinning apparatus for reducing the thickness of absorbent bodies it is preferable that the controller sets the size of the gap in such a manner that the absorbent body that passes through the gap is not sandwiched nor pressed by the pair of rollers, when a thickness indicated by the measurement information is equal to or within a target range of the thickness of the absorbent body.

According to such a thinning apparatus for reducing the thickness of absorbent bodies, the absorbent bodies whose thickness is within the target range are not sandwiched and pressed by the pair of rollers so that defective products caused by the pair of rollers can be certainly prevented from occurring.

In the thinning apparatus for reducing the thickness of absorbent bodies it is preferable that a plurality of the absorbent bodies are transported in line in the transport direction, the sensor outputs the measurement information for each of the absorbent bodies, and the controller sets the size of the gap of the pair of rollers for each of the absorbent bodies while associating the measurement information to each of the absorbent bodies.

According to such a thinning apparatus for reducing the thickness of absorbent bodies, the size of the gap between the pair of rollers is individually set for each absorbent body based on measurement information relating to the thickness output for each absorbent body. Therefore, each thickness of each absorbent body can be brought within the target range in the end even when the thickness of the absorbent body after being sandwiched and pressed with the pressing device varies between each absorbent body.

Further, a method for reducing a thickness of an absorbent body having liquid absorbent fiber as a main material, including:

reducing a thickness of the absorbent body transported in a transport direction, by sandwiching and pressing the absorbent body in a thickness direction orthogonal to the transport direction;

passing the absorbent body through a gap between a pair of rollers that are positioned on a downstream side along the transport direction than the pressing device, and that have outer circumferences of the pair of rollers opposing each other;

outputting by a sensor, measurement information relating to the thickness of the absorbent body at a position between the pressing device and the pair of rollers; and setting a size of the gap based on the measurement information when the absorbent body is passed through the gap between the pair of rollers.

According to such a thinning method for reducing the thickness of absorbent bodies, the size of the gap between the pair of rollers is set based on measurement information relating to the thickness of the absorbent body after being sandwiched and pressed with the pressing device. Therefore, when the thickness of the absorbent body after sandwiching a pressing with the pressing device exceeds the target range, the absorbent body can be thinned by sandwiching and pressing with a pair of rollers and resulting to reduce defective products due to thickness failures of the absorbent body.

Additionally, by thinning the absorbent body with a pair of rollers as above, the thickness of the absorbent body can be kept within the target range so that the pressing apparatus need not be finely adjusted and the number of absorbent articles discarded associated with the adjustment can be reduced.

Present Embodiment

In the present embodiment, the thinning apparatus 20 for reducing the thickness of the absorbent body 1 and method therefor are applied to manufacturing an absorbent body 1 of disposable diapers and sanitary napkins as examples of an absorbent article.

Figure 1A:
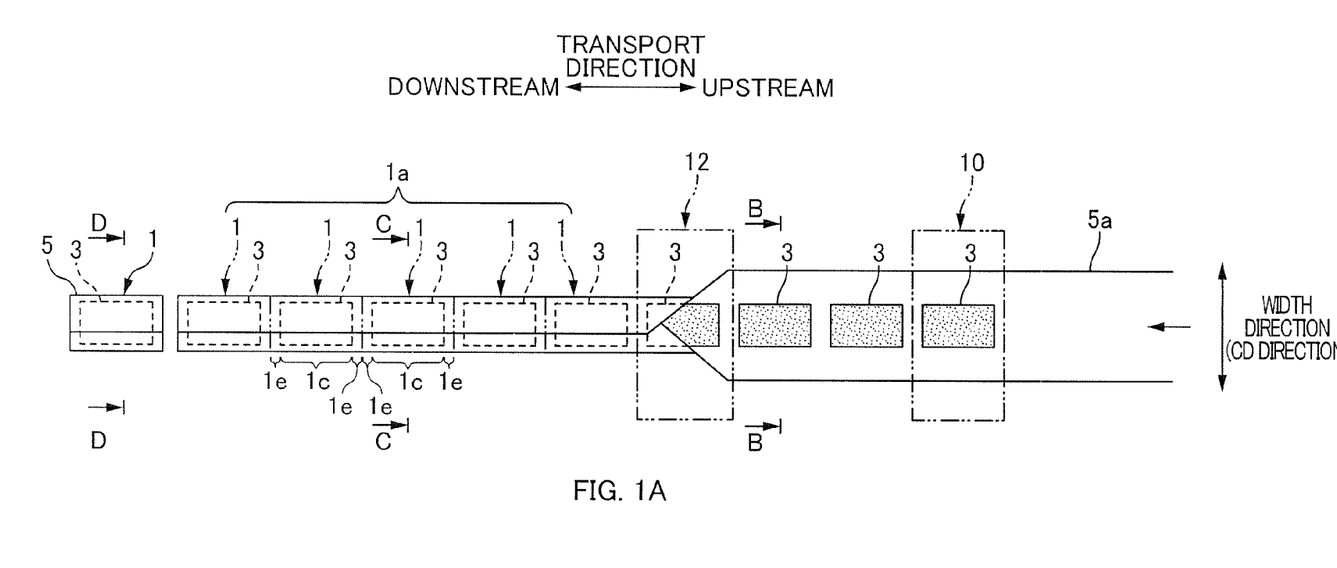
FIG. 1A is a plan view illustrating the manufacturing process of the absorbent body 1.
Figure 1B:
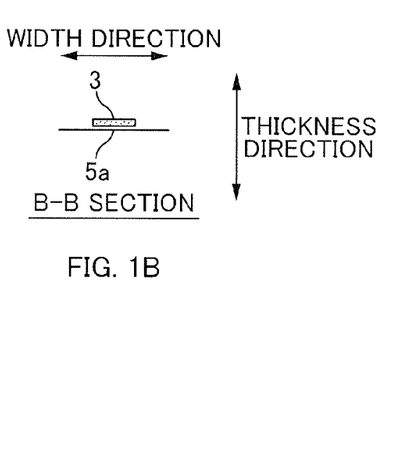
FIG. 1B is a sectional view taken along line B-B of FIG. 1A.
Figure 1C:
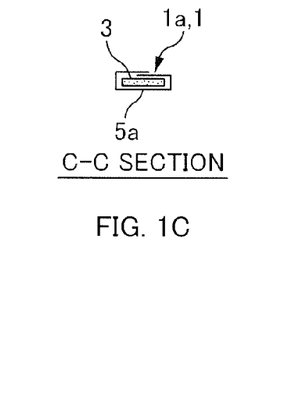
FIG. 1C is a sectional view taken along line C-C of FIG. 1A.
Figure 1D:
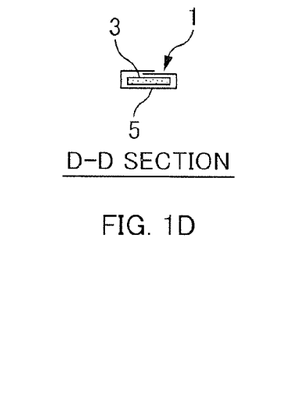
FIG. 1D is a sectional view taken along line D-D of FIG. 1A.

FIGS. 1A to 1D show aspects of the manufacturing process of the absorbent body 1. Note that, FIG. 1A is a planer view and FIGS. 1B, 1C, 1D are sectional views taken along lines B-B, C-C and D-D of FIG. 1A, respectively.

As shown at the leftmost end of FIG. 1A and FIG. 1D, the absorbent body 1 includes an approximately block form layered body 3 having pulp fibers as an example of liquid absorbent fibers layered, whose outer contour is in an approximately rectangular form or an approximately hourglass form and the like seen in a planar view, and a liquid permeable sheet 5 such as tissue paper and the like that covers this layered body 3 over the entire outer circumference. Note that, the layered body 3 may have high-absorbent polymer and the like mixed therein.

Such an absorbent body 1 is manufactured in the following manner.

First, the above liquid permeable sheet 5 is fed as a carrier sheet 5a to the fiber stacking device 10, in a form of a continuous sheet 5a in the transport direction. And the fiber stacking device 10 layers pulp fiber, in approximately block forms intermittently along the transport direction, at approximately the center in the width direction of the surface of the carrier sheet 5a continuously transported along the transport direction (FIG. 1B). Then when this carrier sheet 5a passes by an appropriate location of the folding guide member 12, the end portions in the width direction of this sheet 5a is folded inward in the width direction by this folding guide member 12 and thereby, the surfaces of the plurality of approximately block form layered bodies 3, 3 . . . arranged intermittently along the transport direction are, as shown in FIG. 1C, in states having the end portions in the width direction of the sheet 5a covered. And as a result, there is created a continuous body of absorbent bodies 1a composed of a plurality of absorbent bodies 1, 1 . . . arranged in the transport direction (FIG. 1A).

However, at this point, the absorbent bodies 1, 1 . . . are in hightened states with their thicknesses exceeding the target range (target value plus or minus tolerance). Therefore, the absorbent bodies 1, 1 . . . are sandwiched and pressed in the thickness direction to be thinned by the later described device (not shown in FIG. 1A) of the present embodiment, and thereafter, the continuous body of absorbent bodies 1a is cut into each absorbent body 1 (FIG. 1D) and assembled on another component, as the aforementioned single absorbent body 1.

By the way, the thickness of the absorbent body 1 provided to the continuous body of absorbent bodies 1a is not uniform along the transport direction, but has the first part 1c where the layered body 3 exists shown in FIG. 1A made thick and the second parts 1e, 1e where the layered body 3 does not exist, i.e., the second parts 1e, 1e adjacent in the front and back of the layered body 3 in the transport direction are made thin. To be precise, this means that the part within the absorbent body 1 that is to be made thin is the first part 1c. However, in the following, for the sake of description purposes, thinning of the first part 1c is also referred to as thinning the layered body 1, and the thickness of this first part 1c is also referred to as the thickness of the absorbent body 1.

Figure 2:
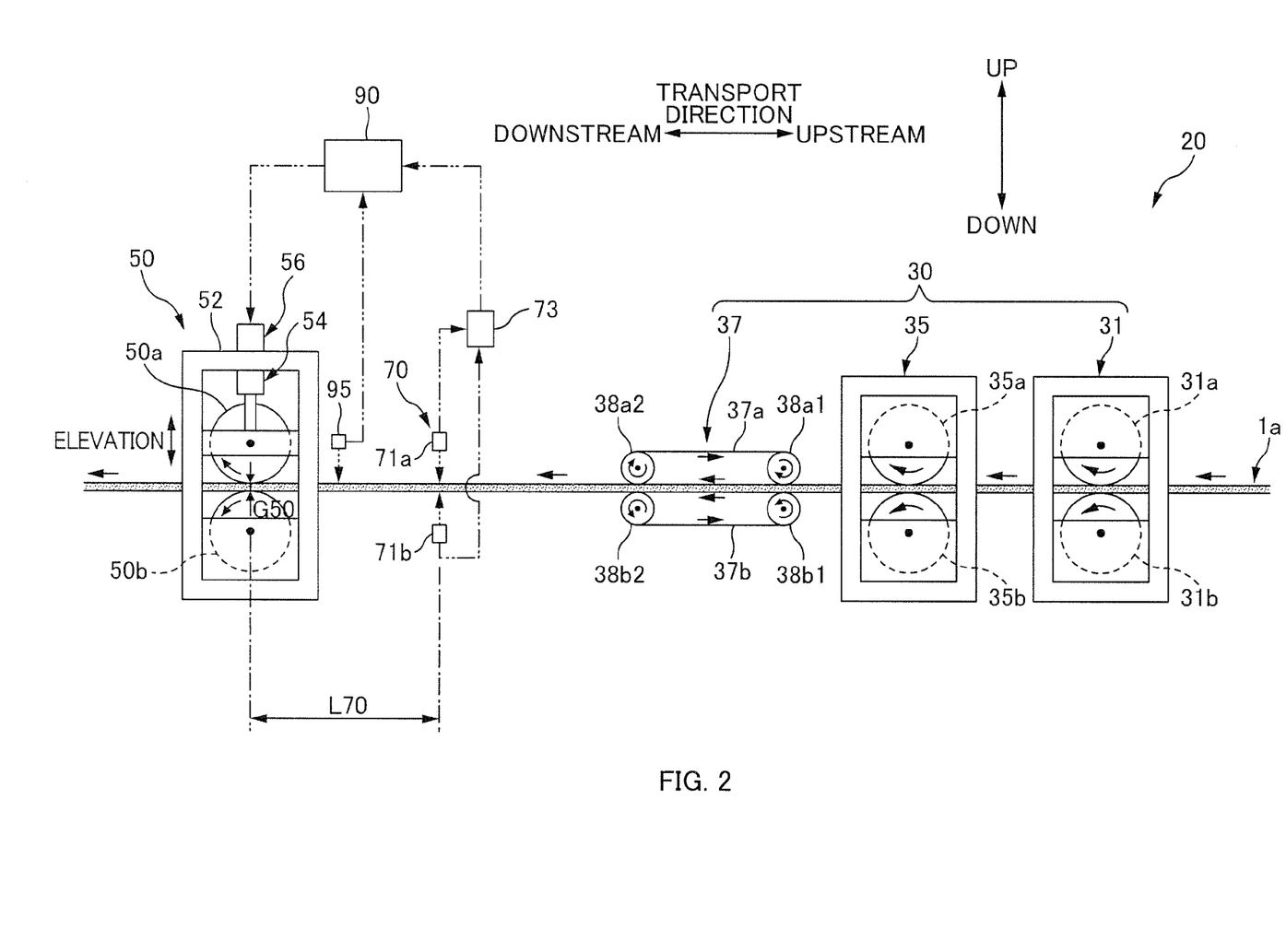
FIG. 2 is a schematic side view of the thinning apparatus 20 for the absorbent body 1 of the present embodiment.

FIG. 2 shows a schematic side view of the thinning apparatus 20 for reducing the thickness of the absorbent body 1 according to the present embodiment. As described above, this apparatus 20 reduces the thickness of the absorbent body 1 to bring the thickness thereof within the target range by sandwiching and pressing the absorbent body 1 in the thickness direction.

This apparatus 20 includes a main pressing device 30 (corresponding to pressing device) that reduces the thickness of the absorbent bodies 1, 1 . . . provided to the continuous body of absorbent bodies 1a, a pair of up-down rollers 50a, 50b as an auxiliary pressing device 50 arranged on the downstream side than the main pressing device 30 along the transport direction, a thickness sensor 70 (corresponding to sensor) that outputs measurement information relating to the thickness of the absorbent body 1 at a position between the main pressing device 30 and the auxiliary pressing device 50, and a controller 90 that sets the size of the gap G50 between the pair of up-down rollers 50a, 50b of the auxiliary pressing device 50.

And the controller 90 sets the size of the above gap G50 (hereinafter, also referred as roller gap G50) of the auxiliary pressing device 50 through which the continuous body of absorbent bodies 1a is to pass, based on the measurement information relating to the thickness of the absorbent body 1 output from the thickness sensor 70.

For example, when the thickness indicated by the measurement information is greater than the target range of the thickness of the absorbent body 1, at the time the target absorbent body 1 corresponding to this measurement information passes through the roller gap G50 of the above auxiliary pressing device 50, the controller 90 sets the size of the above roller gap G50 so that the absorbent body 1 is sandwiched and pressed by the pair of rollers 50a, 50b of this auxiliary pressing device 50. Thereby, the thickness of the absorbent body 1 can be brought within the target range. Further, since the thickness of the absorbent body 1 can be brought within the target range by using the auxiliary pressing device 50 in this way, the main pressing device 30 on the upstream side need not be finely adjusted and further the number of absorbent articles discarded in association with the adjustment can be reduced.

Hereinafter, description of configurations 30, 50, 70, and 90 will be given, however, the direction among the two directions that are orthogonal to the transport direction and that is not in the up-down direction (the direction penetrating the paper in FIG. 2) is also referred to as the CD direction. By the way, this CD direction is parallel to the width direction of the continuous body of absorbent bodies 1a (FIG. 1A) and further the up-down direction is parallel to the thickness direction of the absorbent body 1.

(1) Main Pressing Device 30

In the present embodiment, three different types of pressing devices 31, 35 and 37 are arranged in-line along the transport direction as the main pressing device 30. Each of the absorbent bodies 1, 1 . . . of the continuous body of absorbent bodies 1a are sequentially passed through these three pressing devices 31, 35 and 37 thereby the thickness of the absorbent bodies 1 is thinned in a stepwise manner and hereby, the ripping of the carrier sheet 5a is prevented to prevent scattering of pulp fibers inside the layered body 3 during sandwiching and pressing.

The pressing device 31 located furthest upstream, being the first step, has a pair of up-down rollers 31a, 31b. The rollers 31a, 31b are driven to rotate so to send the absorbent body 1 toward downstream the transport direction while their outer flat surfaces opposing each other with regard to the CD direction. Accordingly when each absorbent body 1 passes through the gap between the rollers 31a, 31b, the pertinent absorbent body 1 is sandwiched and pressed with the outer circumferential surface of the upper roller 31a and the outer circumferential surface of the lower roller 31b in the thickness direction being in the up-down direction, thereby the thickness of the absorbent body 1 is reduced.

The center pressing device 35, being the second step, also has a pair of up-down rollers 35a, 35b, similar to the pressing roller 31 of the first step. However, the outer circumferential surface of roller 35b being one of the pair of rollers 35a, 35b has a flat surface but, the outer circumferential surface of the other roller 35a has formed recessed portions (not shown) of a size slightly larger than the planar form of the first part 1c (FIG. 1A) at this point. And the depth of this recessed portion is less than the thickness of the first part 1c at this point. Therefore, when the absorbent body 1 passes through this pressing device 35, the first part 1c of the absorbent body 1 is covered by the recessed portion while being sandwiched and pressed by this recessed portion and the outer circumferential face of the roller 35b and thereby the thickness of the first part 1c of the absorbent body 1, that is, the thickness of the absorbent body 1 is reduced. Note that, the other configurations besides this are the same as the pressing device 31 of the first step.

The pressing device 37 located furthest downstream, being at the third step, has a pair of up and down endless belts 37a, 37b. And while each endless belt 37a, 37 circles along predetermined circling paths, they transport the absorbent bodies 1 downstream the transport direction while sandwiching and pressing the absorbent bodies 1 with the belt surfaces opposing each other at this time. Therefore, the thickness of the absorbent bodies 1 is reduced while being transported. Note that, the circling path of the upper endless belt 37a is formed by this belt 37a being wound around a pair of rollers 38a1, 38a2 while the circling path of the lower endless belt 37b is formed by this belt 37b being wound around a pair of rollers 38b1, 38b2, and the endless belts 37a, 37b are driven to rotate by at least one of the rollers 38a1, 38a2, 38b1, 38b2 being driven to rotate.

Note that, in the present embodiment, the three types of pressing devices 31, 35, 37 are arranged as the main pressing device 30, however, the manner in which they are arranged is not limited to such and can be changed accordingly. For example, depending on the circumstance, only one pressing device among the above three may be selected and arranged, two or four or more pressing devices may be selected and arranged, or further a plurality of the same type of pressing devices may be combined and arranged.

(2) Auxiliary Pressing Device 50

The auxiliary pressing device 50 is a so-called auxiliary pressing device that sandwiches and presses the absorbent body 1 for reducing the thickness thereof, and allow the thickness of the absorbent body 1 to fall within the target range when the thickness of the absorbent body 1 after passing through the main pressing device 30 exceeds the target thickness range, and has a pair of up-down rollers 50a, 50b as described above. And the rollers 50a, 50b are driven to rotate to send the absorbent bodies 1 downstream along the transport direction with the flat outer surfaces opposing each other with regard to the CD direction. Therefore, when the absorbent body 1 is thinned, the outer circumferential face of the upper roller 50a and the outer circumferential face of the lower roller 50b sandwiches and presses the absorbent body 1 in the up-down direction being the thickness direction of the absorbent body when the absorbent body 1 passes through the roller gap G50 which is the gap between the rollers 50a, 50b.

In this example, the position of the lower roller 50b is fixed by the supporting member 52 such as an appropriate housing and the upper roller 50a is elevatable in the up-down direction being the separating-accessing direction with regard to this lower roller 50b. Therefore, the dimension of the above roller gap G50 is changed by elevating and lowering the upper roller 50a. The elevating mechanism that elevates and lowers the upper roller 50a includes, for example, a feed screw mechanism 54 such as a ball screw provided to the above supporting member 52, and an elevator motor 56 as a drive source for driving this feed screw mechanism 54. Here, the feed screw mechanism 54 converts a rotating movement input thereto to an extending movement in the up-down direction for output. Therefore, the upper roller 50a is made to elevate and descend in accordance to the forward and reverse rotating movement input from the elevator motor 56.

Note that, as the control method for controlling the elevator motor 56 so that the size of the roller gap G50 falls within the target value (set value), a well known position controlling method (for example, servo controlling and the like) that moves the upper roller 50a to the position corresponding to the above target value while detecting the position of the upper roller 50a in the up-down direction and the like with a position detector such as a linear encoder can be applied, and explanation thereof is omitted.

Further, the elevating mechanism is not limited to the aforementioned feed screw mechanism 54 and, for example, a hydraulic cylinder and the like can be applied. And as an example of the hydraulic cylinder in this case, there can be given a hydraulic cylinder and the like equipped with a position detector capable of controlling the extension of the piston based on position control, for example.

(3) Thickness Sensor 70

The thickness sensor 70 is positioned between the pressing device 37 at the third step of the main pressing device 30 and the auxiliary pressing device 50. And the quantity relating to the thickness of the absorbent bodies 1 after sandwiching and pressing with the pressing device 37 at the third step is measured, and thereafter the measurement information is output to the controller 90 for each absorbent body 1.

In this example, the thickness sensor 70 is configured to be capable of directly outputting the thickness of the absorbent body 1 as a quantity relating to thickness. For example, the thickness sensor 70 includes a pair of upper-lower laser rangefinders 71a, 71b and an amplifier 73. And the upper laser rangefinder 71a measures the distance in the vertical direction between the face projected by the sensor head and the surface of the absorbent body 1 and the lower laser rangefinder 71b measures the distance in the vertical direction between the face projected by the sensor head and the lower face of the absorbent body 1, and the measured distance values are sequentially transmitted to the amplifier 73. Each measurement value is respectively subtracted from the measurement value obtained without an absorbent body 1 to calculate the subtracted values and then adds up the subtracted values. Thereafter, the sum value is output to the controller 90 as measurement information of the thickness.

Note that in this example, the thickness sensor 70 includes the above amplifier 73 and the measurement value of the thickness of the absorbent body 1 is output directly from the thickness sensor 70 as measurement information by this amplifier 73 performing the aforementioned calculation, however, the present invention is not limited to such. For example, the controller 90 may be in charge of the function of the amplifier 73 that performs the above calculation. In this case, the thickness sensor 70 would be measuring the distance in the vertical direction between the face projected by the sensor head of the upper laser rangefinder 71a and the surface of the absorbent body 1, and the distance in the vertical direction between the face projected by the sensor head of the lower laser rangefinder 71b and the lower face of the absorbent body 1, to output the measured distance values to the controller 90 as measurement information relating to thickness.

Further, the thickness sensor 70 is not limited to the above laser rangefinders 71a, 71b and an appropriate non-contact displacement gauge such as an ultrasound rangefinder may be applied instead.

(4) Controller 90

The controller 90 controls the elevating movement of the upper roller 50a through controlling the above elevator motor 56 to set the size of the roller gap G50 of the auxiliary pressing device 50 for each absorbent body 1. The controller 90 has an appropriate computer such as a PLC (Programmable Logic Computer), for example, and the computer includes a processor and a memory. And the size of the roller gap G50 is set for each absorbent body 1 through controlling the above elevator motor 56 by the processor reading and executing a program stored in the memory.

The size setting of the roller gap G50 is performed based on measurement information (hereinafter also referred as actual thickness information) of the thickness of the absorbent body 1, sent from the thickness sensor 70.

For example, when the thickness indicated by the actual thickness information exceeds the target range (target value plus or minus tolerance) of the thickness of the absorbent body 1, the controller 90 sets the size of the roller gap G50 so that the absorbent body 1 is sandwiched and pressed when the absorbent body 1 corresponding to the actual thickness information passes through the roller gap G50.

On the other hand, when the thickness indicated by the actual thickness information is within or smaller than the target thickness range of the thickness of the absorbent body 1, the controller 90 sets the size of roller gap G50 so that the absorbent body 1 passing through the roller gap G50 is not sandwiched and pressed.

Figure 3:
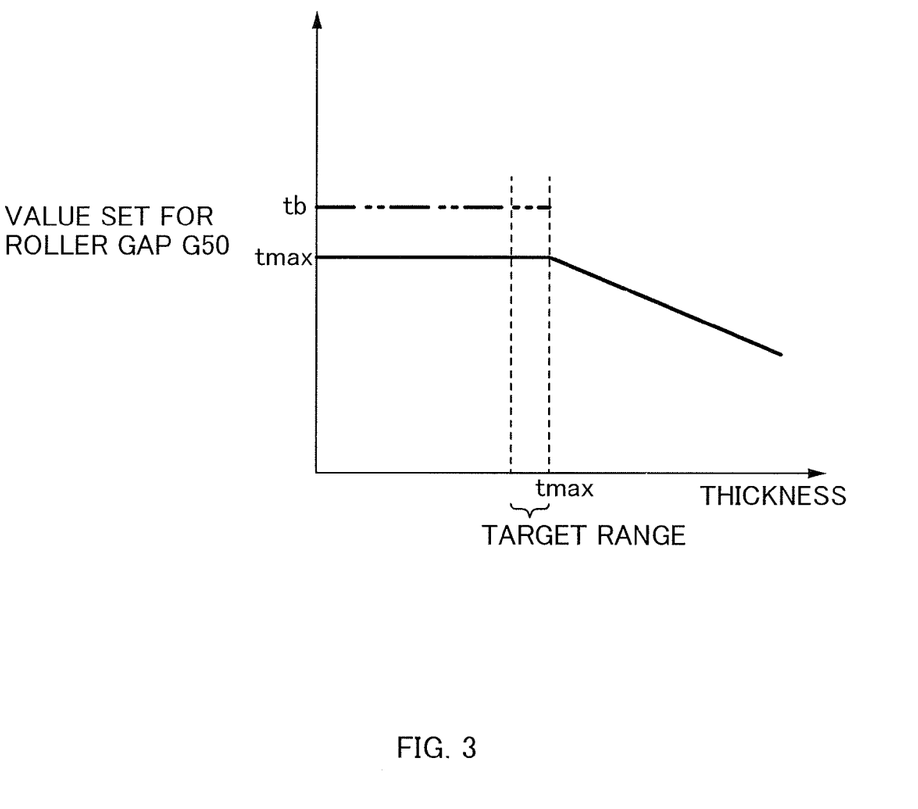
FIG. 3 is a diagram describing the data for setting used when setting the roll gap G50 of the auxiliary pressing device 50.

Data for setting as shown in the graph of FIG. 3, for example, is stored in the memory of the controller 90 in advance in order to perform setting in the above manner. In other words, this memory has stored therein data for setting that indicate the relation between the thickness of the absorbent body 1 at a position between the pressing device 37 at the third step and the auxiliary pressing device 50, and the setting value being the size of the roller gap G50 to be set. Therefore, the processor of the controller 90 refers to the data for setting in FIG. 3 with actual thickness information of the absorbent body 1 transmitted from the thickness sensor 70 as the key, and acquires the value for setting the roller gap G50 corresponding to the thickness of this actual thickness information. And the processor controls the aforementioned elevator motor 56 so that the roller gap G50 between the pair of up-down rollers 50a, 50b is at the set value.

For example, with the data for setting shown in FIG. 3, values among those indicating the thicknesses in the horizontal axis of the graph that are greater than the target range has associated a value set for the roller gap G50 indicated in the vertical axis, that is equal to or smaller than the upper limit value tmax of the target thickness range. Therefore, when the thickness of the actual thickness information exceeds the target range, the auxiliary pressing device 50 certainly sandwiches and presses the absorbent body 1 thereby defects in the thickness of the absorbent bodies 1 can be reduced.

Further, for numerical values greater than the target range in the horizontal axis of FIG. 3, a relation is defined such that the setting value of the roller gap G50 gradually decreases as the thickness in the horizontal axis increases. Therefore, the thickness of the absorbent body 1 after sandwiching and pressing with the auxiliary pressing device 50 can be further certainly brought within the target range, and as a result, thickness defects of the absorbent body 1 can be further reduced.

On the other hand, for numerical values, among the values in the horizontal axis of the graph in FIG. 3 that are within or smaller than the target range has associated, a value set for the roller gap G50 indicated in the vertical axis that is equal to the upper limit value tmax of the target thickness range. Therefore, when the thickness of the actual thickness information is within the target range, the absorbent body 1 only passes through the roller gap G50 of the auxiliary pressing device 50 without the auxiliary pressing device 50 performing sandwiching and pressing, and consequently thickness defects associated with the auxiliary pressing device 50 can be prevented from occurring. However, for numerical values within or smaller than the target range, it is preferable that the setting value of the roller gap G50 is associated with a value tb larger than the maximum value tmax of the target range, as shown with the chain double-dashed line of FIG. 3. In this way, the absorbent body 1 is in a completely non-contact state with the upper roller 50a so that sandwiching and pressing with the auxiliary pressing device 50 can be perfectly prevented.

Further, when the relation of the data for setting in FIG. 3 is variable in accordance with the transport speed of the absorbent body 1, the assumed transport speed of the absorbent body 1 during manufacturing may be divided into a plurality of sections with the above data for setting for each section stored in the memory. Note that in this case, a corresponding data for setting is selected based on the actual value of the transport speed of the absorbent body 1 (for example, the transport speed of the absorbent body 1 at the roller gap G50), and the setting value of the roller gap G50 of the auxiliary pressing device 50 is acquired based on the selected data for setting. By the way, the reason why the relation of the graph shown in FIG. 3 may vary according to the transport speed is that since the time during which the sandwiching and pressing with the auxiliary pressing device 50 is performed differs with differing in transport speed, there is fear that the effect in crushing in the thickness direction of the absorbent body 1 would differ even when the size of the roller gap G50 is the same.

Such data for setting may be stored in the memory of the controller 90 in a format of an arithmetic expression, or may be stored in a setting table format with the thickness of the absorbent body 1 and the setting value for the roller gap G50 in a corresponding state, or further in a state besides the above.

By the way, the continuous body of absorbent bodies 1a according to the present embodiment is configured with a plurality of absorbent bodies 1, 1 ... arranged in the transport direction (FIG. 1A). Further, the thickness sensor 70 outputs actual thickness information for each absorbent body 1 and the auxiliary pressing device 50 sets the size of the roller gap G50 for each absorbent body 1 based on the actual thickness information. Further, the thickness sensor 70 is positioned at a location upstream along the transport direction distant from the auxiliary pressing device 50 by a predetermined distance (FIG. 2).

Therefore, the size setting of the above roller gap G50 needs to be performed while associating the actual thickness information for each absorbent body 1. And this association is performed, for example, in the following manner.

First, the actual thickness information is recorded in the memory of the controller 90 immediately after each output from the thickness sensor 70. Further, each recorded actual thickness information has recorded in association therewith a count value having a predetermined initial value. This predetermined value is, for example, the number of absorbent bodies 1, 1 . . . that can exist within the range L70 between the center position of the auxiliary pressing device 50 and the measuring position of the thickness sensor 70. Further, there is positioned proximate the auxiliary pressing device 50, a passage detecting sensor 95 such as a phototube and the like that outputs at real time a detection signal whenever detecting the tail end (upstream end) of the first part 1c of each absorbent body 1. And the position where detection is made by the passage detecting sensor 95 is set at a position distant, from the center position of the auxiliary pressing device 50, on the upstream side (or the downstream side) by a distance that is equal to an integer multiple (equal to or greater than an integer multiple of two) of the entire length of the absorbent body 1. Note that, substitutional detection is performed by this passage detecting sensor 95 to detect the tail end (upstream end) of the first part 1c of the absorbent body 1 passing through the roller gap G50 of the auxiliary pressing device 50, by setting the entire length to equal an integer multiple.

And the aforementioned count value is subtracted every time the above detection signal is output and when this count value reaches one, the processor of the controller 90 reads from the memory the actual thickness information that takes this count value of one, and sets the size of the roller gap G50 based on this actual thickness information and the aforementioned data for setting. Hereby, the roller gap G50 is set while associating actual thickness information with each absorbent body 1.

Further, the size setting of the roller gap G50 is, for example, performed while the second part 1e of the absorbent body 1 passes through the roller gap G50. That is, the size setting of the roller gap G50 for the absorbent body 1 in subject of setting is performed while the second part 1e of the absorbent body 1 adjacent on the downstream side to the absorbent body 1 in subject to setting, and the second part 1e of the subsequent absorbent body 1 in subject to setting are passing through the roller gap G50. Thereby, the size setting of the roller gap G50 can be certainly completed before the first part 1c of the absorbent body 1 in subject to setting arrives.

And the size of the roller gap G50 that is set, is maintained at a fixed value until the same the first part 1c completely passes through the roller gap G50. In other words, a setting value is given to each absorbent body 1 as a fixed value. Therefore, at this setting, with the actual thickness information of the absorbent body 1 in subject to setting, the processor of the controller 90 calculates the average actual thickness value by averaging the thickness of the first part 1c along the entire length thereof, refers to the data for setting in aforementioned FIG. 3 with the average value as the representative value of the actual thickness, and acquires the value set for the roller gap G50 corresponding to this representative value. And the processor of the controller 90 controls the elevator motor 56 with this single setting value until the first part 1c completely passes through. However, the representative value of the actual thickness is not limited to the aforementioned average value and, for example, the actual thickness of the first part 1c at a point such as that at the center of the plane can be used.

Other Embodiments

While the present invention has been described in conjunction with the embodiments, it should be understood that the present invention is not limited to the above embodiments and can be changed as in the following.

Although the surface of the layered body 3 of the carrier sheet 5 (5a) having the end portions in the width direction of the carrier sheet 5 (5a) covered was shown as an example of the absorbent body 1 in the aforementioned embodiment, the present invention is not limited to such. For example, a carrier sheet 5 (5a) with the end portions in the width direction left in an extended state (see FIG. 1B) without the layered body 3 covered at the ends may be used as the absorbent body 1. Further, the carrier sheet 5 (5a) in such state (FIG. 1B) being covered by a separate liquid permeable sheet from above (not shown) to form a three layer structure with the layered body 3 sandwiched by the liquid permeable sheet and the carrier sheet 5 (5a) can be made the absorbent body 1.

Although the setting value of the roller gap G50 was acquired as a single fixed value for each absorbent body 1 and thereby maintained the size of the roller gap G50 constant along the entire length of the first part 1c of the absorbent body 1, in the aforementioned embodiment, the present invention is not limited to such.

For example, when the aforementioned actual thickness information has respective thickness values that are associated with the positions in the transport direction defined on the absorbent body 1, setting values corresponding to the thicknesses of the positions may be acquired from the data for setting in FIG. 3, to change the size of the roller gap G50 using the setting value corresponding to each position in synchronization with the passage of each position through the roller gap G50. Note that, the generation of the actual thickness information as that above is made by, for example, acquiring data of the above positions by an output signal from a rotary encoder that makes a single rotation for an amount of transport for a single absorbent body 1, and recording into the memory of the controller 90 the thickness value that is output from the thickness sensor, in association with the position data, simultaneously with the acquiring of data of the positions. Further, each position detection of the absorbent body 1 passing through the roller gap G50 is, for example, performed based on the output signal from the rotary encoder rotating in synchronization with the roller 50a (or 50b) of the auxiliary pressing device 50, and the same processor sequentially acquires from the above actual thickness information, the thickness value corresponding to the position indicated by this output signal. Then, the setting value corresponding to the thickness value is obtained by referring to the data for setting in FIG. 3, and thereafter the size of the roller gap G50 is sequentially set.

A sensor for measuring the thickness of the absorbent body 1 was not set on the downstream side of the auxiliary pressing device 50 in the aforementioned embodiment, however, a sensor may be provided to the position on the downstream side of the auxiliary pressing device 50 to measure with this sensor the thickness of the absorbent body 1 after passing through the auxiliary pressing device 50. In this case, the sensor can have, for example, applied thereto a configuration same as that with the aforementioned thickness sensor 70 provided at the upstream side of the auxiliary pressing device 50. And the measurement information is, for example, sequentially transmitted to the controller 90 where the controller 90 compares the measurement information with the thickness target range to, for example, output an alarm when the thickness is outside the target, which is used to identify thickness defects.

REFERENCE SIGNS LIST 1 absorbent body, 1a continuous body of absorbent bodies,
1c first part,
1e second part,
3 layered body,
5 liquid permeable sheet, 5a carrier sheet,
10 fiber stacking device, 12 folding guide member,
20 thinning apparatus for reducing the thickness of absorbent body,
30 main pressing device (pressing device),
31 first step pressing device, 31a roller, 31b roller,
35 second step pressing device, 35a roller, 35b roller,
37 third step pressing device, 37a endless belt, 37b endless belt,
38a1 roller, 38a2 roller, 38b1 roller, 38b2 roller,
50 auxiliary pressing device, 50a roller, 50b roller, 52 supporting member,
54 elevating mechanism, 56 elevator motor,
70 thickness sensor (sensor), 71a laser rangefinder, 71b laser rangefinder,
73 amplifier,
90 controller, 95 passage detecting sensor,
G50 roller gap (gap)

The invention claimed is:

1. An apparatus for reducing a thickness of absorbent bodies of a continuous body, the absorbent bodies having liquid absorbent fibers as a main material, said apparatus comprising:
a pressing device configured to reduce the thickness of the absorbent bodies of the continuous body transported in a transport direction, by sandwiching and pressing the absorbent bodies of the continuous body in a thickness direction orthogonal to the transport direction, wherein each of the absorbent bodies has:
a first part having a layered body, and
a second part free of the layered body;
a pair of rollers positioned on a downstream side of the pressing device along the transport direction, and configured to rotate while passing the continuous body through a gap formed by outer circumferences of the pair of rollers opposing each other;
a sensor configured to output measurement information relating to the thickness of the absorbent bodies of the continuous body at a position between the pressing device and the pair of rollers; and
a controller configured to set a size of the gap between the pair of rollers based on the measurement information, wherein
the controller is configured to set the size of the gap in such a manner that the absorbent bodies of the continuous body pass through the gap while being sandwiched and pressed by the pair of rollers, when a thickness indicated by the measurement information is greater than a target range of the thickness of the absorbent bodies of the continuous body, and
the controller is further configured to set the size of the gap while the second part is passing through the gap and to complete setting of the size of the gap before the first part arrives at the gap.

2. An apparatus for reducing a thickness of absorbent bodies of a continuous body, said absorbent bodies having liquid absorbent fibers as a main material, said apparatus comprising:
a pressing device configured to reduce the thickness of the absorbent bodies of the continuous body transported in a transport direction, by sandwiching and pressing the absorbent bodies of continuous body in a thickness direction orthogonal to the transport direction, wherein each of the absorbent bodies has:
a first part having a layered body, and
a second part free of the layered body;
a pair of rollers positioned on a downstream side of the pressing device along the transport direction, and configured to rotate while passing the continuous body through a gap formed by outer circumferences of the pair of rollers opposing each other;
a sensor configured to output measurement information relating to the thickness of the absorbent bodies of the continuous body at a position between the pressing device and the pair of rollers; and
a controller configured to set a size of the gap between the pair of rollers based on the measurement information, wherein
the controller is configured to set the size of the gap in such a manner that the absorbent bodies of the continuous body pass through the gap without being pressed by the pair of rollers, when a thickness indicated by the measurement information is equal to or within a target range of the thickness of the absorbent bodies of the continuous body, and
the controller is further configured to set the size of the gap while the second part is passing through the gap and to complete setting of the size of the gap before the first part arrives at the gap.

3. The apparatus according to claim 1, wherein
the apparatus is configured to transport the absorbent bodies sequentially in the transport direction,
the sensor is configured to output the measurement information for each of the absorbent bodies, and
the controller is configured to set the size of the gap of the pair of rollers for each of the absorbent bodies while associating the measurement information to each of the absorbent bodies.

4. A method of reducing a thickness of absorbent bodies of a continuous body, said absorbent bodies having liquid absorbent fibers as a main material, said method comprising:
reducing a thickness of the absorbent bodies of the continuous body transported in a transport direction, by sandwiching and pressing, by a pressing device, the absorbent bodies of the continuous body in a thickness direction orthogonal to the transport direction, wherein each of the absorbent bodies has:
a first part having a layered body, and
a second part free of the layered body;
passing the continuous body through a gap between a pair of rollers opposing each other and positioned on a downstream side of the pressing device along the transport direction;
outputting, by a sensor, measurement information relating to the thickness of the absorbent bodies of the continuous body at a position between the pressing device and the pair of rollers; and
setting, by a controller, a size of the gap based on the measurement information when the absorbent bodies of the continuous body are passed through the gap between the pair of rollers, wherein the controller sets the size of the gap in such a manner that the absorbent bodies of the continuous body pass through the gap while being sandwiched and pressed by the pair of rollers, when a thickness indicated by the measurement information is greater than a target range of the thickness of the absorbent bodies of the continuous body, and the controller sets the size of the gap while the second part is passing through the gap and completes setting of the size of the gap before the first part arrives at the gap.

5. A method of reducing a thickness of absorbent bodies of a continuous body, said absorbent bodies having liquid absorbent fibers as a main material, said method comprising:

reducing a thickness of the absorbent bodies of the continuous body transported in a transport direction, by sandwiching and pressing, by a pressing device, the absorbent bodies of the continuous body in a thickness direction orthogonal to the transport direction, wherein each of the absorbent bodies has:
- a first part having a layered body exists, and
- a second part free of the layered body;

passing the continuous body through a gap between a pair of rollers opposing each other and positioned on a downstream side of the pressing device along the transport direction;

outputting, by a sensor, measurement information relating to the thickness of the absorbent bodies of the continuous body at a position between the pressing device and the pair of rollers; and setting, by a controller, a size of the gap based on the measurement information when the absorbent bodies of the continuous body are passed through the gap between the pair of rollers, wherein the controller sets the size of the gap in such a manner that the absorbent bodies of the continuous body pass through the gap without being pressed by the pair of rollers, when a thickness indicated by the measurement information is equal to or within a target range of the thickness of the absorbent bodies of the continuous body, and the controller sets the size of the gap while the second part is passing through the gap and completes setting of the size of the gap before the first part arrives at the gap.

6. The apparatus according to claim 1, wherein the controller is configured to set the size of the gap in such a manner that absorbent bodies of the continuous body pass through the gap without being pressed by the pair of rollers, when a thickness indicated by the measurement information is equal to or within a target range of the thickness of the absorbent bodies of the continuous body.

7. The method according to claim 4, wherein the controller sets the size of the gap in such a manner that the absorbent bodies of the continuous body pass through the gap without being pressed by the pair of rollers, when a thickness indicated by the measurement information is equal to or within a target range of the thickness of the absorbent bodies of the continuous body.

\* \* \* \* \*